United States Patent [19]
Fechtel et al.

[11] Patent Number: 5,744,618
[45] Date of Patent: Apr. 28, 1998

[54] PROCESS FOR THE PREPARATION OF ASCORBIC ACID

[75] Inventors: Ulrich Fechtel, Ober-Ramstadt; Karlheinz Wembacher, Pfungstadt, both of Germany

[73] Assignee: Merck Patent Gesellschaft Mit Beschrankter Haftung, Darmstadt, Germany

[21] Appl. No.: 766,276

[22] Filed: Dec. 13, 1996

[30] Foreign Application Priority Data

Dec. 16, 1995 [DE] Germany .................. 195 47 073.7

[51] Int. Cl.$^6$ ............................................. C07D 307/62
[52] U.S. Cl. ............................................. 549/315
[58] Field of Search ............................................. 549/315

[56] References Cited

U.S. PATENT DOCUMENTS 5,637,734  6/1997  Honda et al. .................. 549/315

FOREIGN PATENT DOCUMENTS 2 205 567  12/1988  United Kingdom.

OTHER PUBLICATIONS

Jurgen Falbe, Carbonsauren und Carbonsaure–Derivate, Jun. 28, 1985, pp. 671–672.

*Primary Examiner*—Johann Richter
*Assistant Examiner*—Laura L. Stockton
*Attorney, Agent, or Firm*—Millen, White, Zelano, & Branigan, P.C.

[57] ABSTRACT

A process for the preparation of L-ascorbic acid by reacting 2-keto-L-gulonic acid with aqueous mineral acid in a solvent mixture containing an inert organic solvent, an aliphatic ketone and also an acid chloride.

7 Claims, No Drawings

PROCESS FOR THE PREPARATION OF ASCORBIC ACID

BACKGROUND OF THE INVENTION

The invention relates to a process for the preparation of L-ascorbic acid by reacting 2-keto-L-gulonic acid with aqueous mineral acid in a solvent mixture containing an inert organic solvent and an aliphatic ketone, wherein an acid chloride is added.

The invention relates in particular to a process for the preparation of L-ascorbic acid, wherein a mixture consisting of 2-keto-L-gulonic acid, an inert solvent, a ketone and an aqueous mineral acid is heated and subsequently an acid chloride is added.

Processes for the preparation of ascorbic acid in one step by reacting 2-keto-L-gulonic acid with an acid are known. In U.S. Pat. No. 2,185,383, the reaction of 2-keto-L-gulonic acid with concentrated hydrochloric acid and acetic acid as solvent is described. In the unexamined Japanese Application 58-177,986, a process for the preparation of L-ascorbic acid is described, in which initially a solution of sodium 2-keto-L-gulonic acid in ethanol and acetone is neutralized with hydrochloric acid. In the examined Japanese Application 48-15,931, the reaction of 2-keto-L-gulonic acid with a mineral acid in an inert solvent in the presence of a surface-active substance is described. In the same way, the preparation of L-ascorbic acid starting from 2-keto-L-gulonic acid anhydride in the presence of a surface-active substance is described in WO 87/00839. In EP 0,324,261 and in GB 2,205,567, the reaction of 2-keto-L-gulonic acid with an acid in a mixture of inert solvents in the presence of a surface-active substance is described.

SUMMARY OF THE INVENTION

Surprisingly, investigations in the field of the synthesis of L-ascorbic acid have shown that, if acid chlorides are added, surface-active substances can be omitted. The novel process according to the invention makes it possible to obtain L-ascorbic acid by lactonization of 2-keto-L-gulonic acid with aqueous mineral acid in a solvent mixture with addition of the acid chloride in high yields which are no lower than those in the processes already known. This is demonstrated by a comparative experiment which was carried out in accordance with the statements of the ingredients in GB 2,205,567.

By means of the acid chloride, a part of the water in the system can be removed and an influence can thus be exerted on the water content and hence on the yield of ascorbic acid.

The process according to the invention also proves to be advantageous with respect to the quantities which can be employed. Thus, it is possible to operate with a substantially greater quantity (2–4 times) of ketogulonic acid per unit volume, yields of over 90% of theory being realized (Illustrative Example 2).

The solvent mixture consists of an inert solvent and an aliphatic ketone, the ketone/inert solvent ratio being variable within a wide range. For example, the ketone can be added in an equal quantity relative to the inert solvent. Preferably, 0.02–0.3% by volume of ketone, particularly preferably 0.03–0.1% by volume, is added relative to 1% by volume of the inert solvent.

Examples of suitable inert solvents are hydrocarbons such as hexane, heptane, octane, petroleum ether, benzene, toluene or xylene; chlorinated hydrocarbons such as chlorobenzene, trichloroethylene, 1,2-dichloroethane, carbon tetrachloride, chloroform or dichloromethane; ethers such as tetrahydrofuran, dioxane or isopropyl ether, if appropriate also mixtures of the solvents with one another. Aliphatic ketone means preferably acetone, methyl ethyl ketone, diethyl ketone, methyl isopropyl ketone and also cyclohexyl ketone.

The invention also relates to a process characterized in that 0.01 to 1 part of acid chloride relative to 1 part of inert solvent is employed. Particularly preferred is a ratio of 0.1 to 0.4 part of acid chloride relative to 1 part of inert solvent. A ratio of 0.01 to 0.2 part of acid chloride relative to 1 part of 2-keto-L-gulonic acid is also preferred.

The invention also relates to a process, as described above, in which the acid chloride is an aliphatic carboxylic acid chloride having 1 to 4 C atoms, in particular acetyl chloride, propionyl chloride, phosgene, diphosgene, oxalyl chloride and also malonic acid dichloride, succinic acid dichloride or butyryl chloride.

The acid chloride preferably is also thionyl chloride and also phosphorus oxychloride.

The reaction of 2-keto-L-gulonic acid is carried out in a solvent mixture as described above. The concentration of 2-keto-L-gulonic acid relative to the solvent mixture is not restricted. 5–40 per cent by weight of 2-keto-L-gulonic acid is preferred.

The aqueous mineral acid is, for example, hydrochloric acid, phosphoric acid or sulphuric acid. Preferably, 0.2 to 2 mol of mineral acid relative to 1 mol of 2-keto-L-gulonic acid is employed.

The invention also relates to a process, as described, characterized in that the reaction is carried out at temperatures between 40° and 100° C. Preferred is the temperature range between 50° and 80° C., and the temperature range between 55° and 70° C. is very particularly preferred.

The working-up is carried out by methods known per se, for example by filtration, removal of the solvent, extraction and/or crystallization. According to the process of the invention, the yields of L-ascorbic acid are as a rule above 90%, so that involved purification steps can be omitted. Above and below, all temperatures are indicated in °C. The determinations of content (purity), were carried out, for example, by iodometric determination of the ascorbic acid content in the crude product considered by mass.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application(s) German DE 195 47 073.7, are hereby incorporated by reference.

EXAMPLES

Example 1

30 ml of acetone and 18.3 ml of 37% hydrochloric acid are added to a solution of 100 g of 2-keto-L-gulonic acid (97.7%, 2.3% of water) in 575 ml of toluene, and the mixture is heated for 1 hour at 60° C. A mixture consisting of 9.4 ml of acetyl chloride and 50 ml of acetone is then added and the mixture is kept for 7 hours at 60°. The hydrochloric acid is removed by distillation. The solid which has arisen is filtered off, and the filter cake is rinsed with 50 ml of toluene and dried. This gives 85.9 g of L-ascorbic acid; purity: 94.6%; yield: 91.7% of theory.

Example 2

A solution of 200 g of 2-keto-L-gulonic acid (97.7%, 2.3% of water) in 170 ml of toluene, 80 ml of acetone and 20 ml of 37% HCl is heated for 2 hours at 60○. A mixture consisting of 18.8 g of acetyl chloride in 40 ml of acetone and 16.6 ml of 37% HCl in 40 ml of acetone is then added and the mixture is kept for 7 hours at 60○. The working-up is carried out analogously to Example 1. This gives 170.4 g of ascorbic acid; purity 94.4%; yield: 91.4% of theory.

Example 3

A solution of 100 g of 2-keto-L-gulonic acid (97.7%, 2.3% of water) in 570 ml of toluene, 30 ml of acetone and 10 ml of 37% HCl is heated for 1 hour at 60°. A mixture consisting of 8.8 of thionyl chloride in 50 ml of acetone and 6.7 ml of 37% HCl is then added and the mixture is kept for 4 hours at 60°. The working-up is carried out analogously to Example 1. This gives 86.3 g of ascorbic acid; purity 94.4%; yield: 91.9% of theory.

Example 4

A solution of 100 g of 2-keto-L-gulonic acid (97.7%, 2.3% of water) in 575 ml of toluene, 30 ml of acetone and 10 ml of 37% HCl is heated for 3 hours at 60°. A mixture consisting of 7.3 g of diphosgene in 50 ml of acetone and 7.0 ml of 37% HCl is then added and the mixture is kept for 8 hours at 60°. The working-up is carried out analogously to Example 1. This gives 85.0 g of ascorbic acid; purity 95.4%; yield: 91.5% of theory.

Comparative Experiment

A solution of 100 g of 2-keto-L-gulonic acid in 575 ml of toluene, 30 ml of acetone and 10 ml of 37% HCl is heated for 3 hours at 60°. A mixture consisting of 5.4 g of distilled water, 10 ml of 37% hydrochloric acid, 0.117 g of N-cetyl-N,N,N-trimethylammonium bromide and 52.2 g of HCl/acetone (22.2%) is then added and the mixture is kept for 8 hours at 60°. The working-up is carried out analogously to Example 1. This gives 85.4 g of ascorbic acid; purity 93.5%; yield 90.1% of theory.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of L-ascorbic acid by reacting 2-keto-L-gulonic acid with aqueous mineral acid in a solvent mixture containing an inert organic solvent and an aliphatic ketone, characterized in that an acid chloride is added to said solvent mixture.

2. A process according to claim 1, wherein 0.01 to 1 part of acid chloride relative to 1 part of said inert organic solvent is employed.

3. A process according to claim 1, wherein the reaction is carried out at temperatures between 40° and 100° C.

4. A process according to claim 1, wherein a mixture consisting of 2-keto-L-gulonic acid, an inert solvent, a ketone and an aqueous mineral acid is heated and subsequently an acid chloride is added to said solvent mixture.

5. A process according to claim 1, wherein the acid chloride is an aliphatic carboxylic acid chloride having 1 to 4 C atoms.

6. A process according to claim 1, wherein the acid chloride is thionyl chloride.

7. A process according to claim 5, wherein the acid chloride is an aliphatic carboxylic acid chloride selected from the group comprising acetyl chloride, oxalyl chloride, phosgene and diphosgene.

* * * * *